United States Patent [19]

Hardtmann

[11] 3,994,918
[45] Nov. 30, 1976

[54] SPIRO(5H-DIBENZO[a,d]CYCLOHEPTEN-5-OXAZOLIN-2-ONES) AND THEIR 10,11-DIHYDRO DERIVATIVES

[75] Inventor: Goetz E. Hardtmann, Florham Park, N.J.

[73] Assignee: Sandoz, Inc., East Hanover, N.J.

[22] Filed: June 17, 1975

[21] Appl. No.: 587,534

Related U.S. Application Data

[60] Division of Ser. No. 23,077, March 26, 1970, Pat. No. 3,911,017, which is a continuation-in-part of Ser. No. 813,700, April 4, 1969, abandoned.

[52] U.S. Cl. ............................................. 260/307 C
[51] Int. Cl.$^2$ ..................................... C07D 263/22
[58] Field of Search .................................. 260/307 C

[56] References Cited
OTHER PUBLICATIONS

Cope et al., J. Am. Chem. Soc., 78, 1012–1013 (1956).

Primary Examiner—Raymond V. Rush
Attorney, Agent, or Firm—Gerald D. Sharkin; Richard E. Vila

[57] ABSTRACT

The invention discloses compounds of the class of 5-substituted-5H-dibenzo[a,d]cycloheptenes which are 5-hydrazinoalkyl- or 5-aminoalkyl-5H-dibenzo[a,d]cyclohepten-5-ols, or their 10,11-dihydro derivatives. The compounds are pharmaceutically active and useful, for example, as anti-convulsants and tranquilizers. A key intermediate are compounds which are a spiro[-5H-dibenzo[a,d]cyclohepten-5-oxazolin-2-one] which are subjected to alkaline hydrolysis to obtain the compounds of the invention.

10 Claims, No Drawings

SPIRO(5H-DIBENZO[a,d]CYCLOHEPTEN-5-OXAZOLIN-2-ONES) AND THEIR 10,11-DIHYDRO DERIVATIVES

This application is a division of application Ser. No. 23,077, filed March 26, 1970, now U.S. Letter Pat. No. 3,911,017, which is a continuation-in-part of abandoned application Ser. No. 813,700, filed April 4, 1969.

The present invention relates to 5-substituted-5H-dibenzo [a,d]cycloheptenes including the 10,11-dihydro derivatives. The invention also relates to pharmaceutical methods and compositions utilizing said compounds, and to methods of preparation of said compounds.

The compounds of the present invention are represented by the following structural formula I:

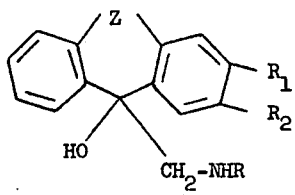

wherein
Z is —CH=CH— or —CH$_2$—CH$_2$—,
R is hydrogen, amino or lower alkyl of 1 to 4 carbon atoms,
R$_1$ is hydrogen, halo of atomic weight of from 19 to 80, or alkoxy of 1 to 3 carbon atoms, and
R$_2$ is hydrogen, halo of atomic weight of from 19 to 80 or alkoxy of 1 to 3 carbon atoms.

Certain of the compounds of formula I may be prepared by reacting in a Step A a compound of the formula II:

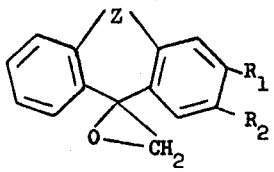

wherein Z, R$_1$ and R$_2$ are as defined, with a nitrogen compound of the formula III:

R°-NH$_2$ wherein R° is hydrogen or amino, i.e. ammonia or hydrazine, whereby there is obtained the compounds of the invention of formula IA:

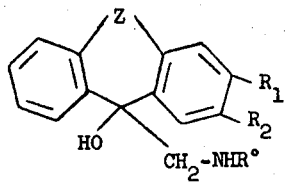

wherein Z, R°, R$_1$ and R$_2$ are as defined.

The compounds I in which R is hydrogen are, however, preferably prepared in a Step A-1 by catalytic hydrogenation of a compound I in which R is amino.

The preparation of compounds of formula IA by Step A involving the reaction of a compound II with a compound III may be carried out at elevated temperatures in the range of 50° C. to 180° C., preferably 80° C. to 130° C. The reaction is conveniently carried out employing an excess of compound III as the reaction medium, especially when compound III is hydrazine. The reaction may also be carried out under pressure as may be desired or required, for example, to maintain the compound III in liquid phase. If desired, various organic solvents of well known type providing an inert solvent medium may be also employed. The reaction product of formula IA may be isolated from the Step A reaction mixture by working up in a known manner.

The preparation of compounds I in which R is hydrogen by Step A-1 involving hydrogenation of a compound I in which R is amino is suitably a catalytic hydrogenation of known type carried out at temperatures in the range of 0° C. to 80° C., preferably 15° C. to 40° C. The more preferred catalyst is platinum metal which may be conveniently formed in-situ from platinum dioxide. Among other catalysts one might also mention palladium supported on carbon, e.g., a catalyst of 3–10% palladium supported on 90–99% of charcoal. The hydrogenation is carried out in an inert organic solvent of conventional type for such hydrogenation reaction, preferably acetic acid. The resulting reaction product of formula I in which R is hydrogen may be isolated from the Step A-1 reaction mixture by working up in a known manner.

Another process for the preparation of certain compounds of the formula I involves subjecting in a Step B reaction a compound of the formula IV:

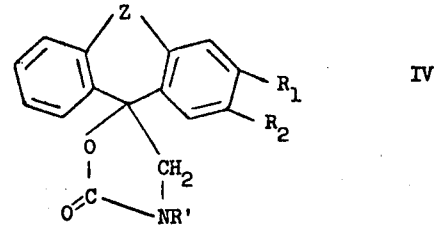

wherein Z, R$_1$ and R$_2$ are as defined and R' is hydrogen or alkyl of 1 to 4 carbon atoms, to alkaline hydrolysis whereby there is obtained compounds of the invention of the formula IB:

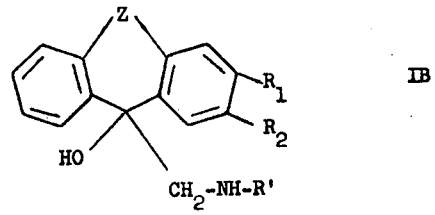

wherein Z, R', R$_1$ and R$_2$ are as defined.

The Step B reaction is suitably carried out at temperatures in the range of from 30° C. to 120° C., preferably 50° C. to 100° C., and preferably in the presence of an inert organic solvent. The alkaline conditions for the reaction may be established in a conventional manner, preferably by employing an alkali metal hydroxide, e.g., sodium hydroxide or potassium hydroxide. Any of several conventional organic solvents may be suitably employed. The preferred solvents are those readily miscible with water including particularly the lower alcohols, e.g. ethanol. The reaction product of formula IB may be isolated from the Step B reaction mixture by working up by established procedures.

The compounds of formula IV in which R' is hydrogen are preferably prepared by subjecting a compound of the formula V:

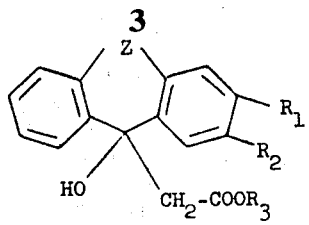

V wherein Z, $R_1$ and $R_2$ are as defined and $R_3$ is lower alkyl of 1 to 4 carbon atoms, to reaction with hydrazine to obtain the compound of the formula VI:

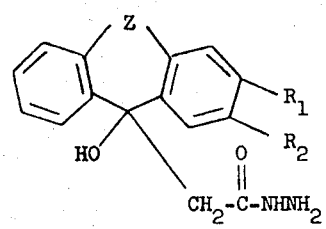

VI wherein Z, $R_1$ and $R_2$ are as defined, said compound VI then being subjected to a cyclization rearrangement to obtain the compound of formula IV.

The preparation of the compound VI from compound V and hydrazine is suitably carried out at temperatures in the range of 40° C. to 150° C., preferably 70° C. to 120° C. The reaction is conveniently carried out employing an excess of hydrazine as the reaction medium although it will be evident that various inert organic solvents of well known type may be employed if desired. The reaction product of formula VI may be isolated from the reaction mixture by working up in a known manner.

The preparation of the compound IV from the compound VI may be carried out at temperatures in the range of from minus 10° C. to 30° C., preferably 0° C. to 20° C. The reaction involves Curtius rearrangement followed by a cyclization and is carried out in an acidic aqueous medium employing a metal nitrite, preferably an alkali metal nitrite such as sodium nitrite or potassium nitrite. The acidic conditions are preferably established employing a lower carboxylic acid such as acetic acid which also serves as a co-solvent. The reaction product of formula IV may be isolated by working up of the reaction mixture by known procedures.

The compounds of formula IV in which R' is alkyl are preferably prepared from the corresponding compound of formula IV in which R' is hydrogen by subjecting the latter in the form of a metallo salt to alkylation in a known manner employing a corresponding alkyl halide of the formula VII:

R''-X  VII wherein R'' is alkyl of 1 to 4 carbon atoms and X is halo, preferably iodo.

The metallo derivatives of the compounds of formula IV in which R' is hydrogen are readily prepared in a known manner by treating the corresponding compound IV in which R' is hydrogen with a conventional agent commonly employed for preparation of such salt which is desirably an alkali metal salt, such agents including sodium hydride and the alkali metal alkoxides of sodium and potassium, preferably sodium hydride. The preparation of the salt may be suitably carried out in any of the suitable conventional inert organic solvents and suitably at temperatures in the range of from 0° C. to 60° C., preferably at about room temperature. Representative of the preferred solvents are dimethylacetamide, diethylacetamide, dimethylformamide and dioxane. The conversion of the metallo derivative to the desired compound IV in which R' is alkyl by reaction of the metallo derivative with a compound of formula VII may be carried out in a conventional manner at temperatures in the range of from 0° C. to 100° C., preferably at about room temperature. The reaction is preferably carried out in an inert organic solvent which conveniently is the solvent in which the metallo salt is prepared. The resulting product may be isolated by working up of the reaction mixture by conventional procedures.

The compounds of formula V employed as starting material herein are of known type and may be prepared from the corresponding dibenzo[a,d]cyclo-hepten-5-one by known procedures. For example, the compounds V in which Z is —CH=CH— may be prepared from the corresponding dibenzo[a,d]cyclo-hepten-5-one by the well-known Reformatsky reaction as illustrated herein in Example 5. The compounds of formula V in which Z is —CH$_2$—CH$_2$— may be prepared from the corresponding 10,11-dihydrodibenzo[a,d]cyclo-hepten-5-one employing a branched chain lower alkyl acetic acid ester in the presence of a strong base such as diethylamino magnesium bromide such that $R_3$ in compound V will be a branched chain lower alkyl, e.g. t-butyl, in accordance with the known technology applied in the preparation of such compounds.

The compounds of formula II in which Z is —CH=CH— are known and the preparation described, for example, in J. Med. Chem. 10, 633, and illustrated hereinafter in Example 1. The compounds of formula II in which Z is —CH$_2$—CH$_2$— are novel compounds which may be prepared in accordance with this invention by subjecting a compound of the formula VIII:

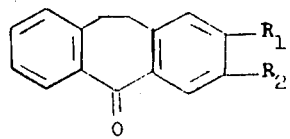

VIII wherein $R_1$ and $R_2$ are as defined, to reaction with dimethylsulphonium methylide of formula IX, (CH$_3$)$_2$S$^+$ = CH$_2^-$  IX in an organic solvent which is inert under the reaction conditions, whereby the compounds of formula II in which Z is —CH$_2$—CH$_2$— and $R_1$ and $R_2$ are as defined are obtained.

The reaction of a compound VIII with the compound IX is suitably carried out at a temperature of from 0° to 40° C., employing dimethylsulphoxide alone or in combination with an ether such as diethyl ether or tetrahydrofuran as the solvent. The compound of formula IX tends to be unstable and is thus preferably prepared in situ. It may be prepared in conventional manner by reaction of trimethylsulphonium iodide, preferably in dimethyl sulphoxide, with a solution of the methylsulphinyl carbanion in tetrahydrofuran, under an inert e.g. nitrogen, atmosphere, and at a temperature of from 0° to 10° C., preferably 0° to 5° C. The solution of the methylsulphinyl carbanion may be produced in conventional manner by reaction of sodium hydride with dimethylsulphoxide at an elevated temperature, and dissolution of the reaction product in tetrahydrofuran. The reaction product of formula II in which Z is —CH$_2$—CH$_2$— may be isolated from the reaction mixture for use in subsequent preparations by working up by conventional procedures.

The various dibenzo[a,d]cyclohepten-5-ones employed as starting material in preparation of compounds II and V are either known per se or may be prepared from known materials by established procedures.

The compounds of formula I may form acid addition salts, and may be produced and isolated as such acid addition salts, as desired or required. It will be evident that pharmaceutically acceptable acid addition salts not materially affecting the pharmacological effect of compounds I are also within the scope of the present invention. Such pharmaceutically acceptable salts may include, by way of illustration, the hydrochloride, fumarate, maleate, formate, acetate, benzoate, sulfonate, methanesulfonate and malonate. The acid addition salts of the subject compound I may be produced from the corresponding free bases by conventional procedures. Conversely, the free bases may be obtained from the salts by procedures known in the art.

The compounds of formula I are useful because they possess pharmacological activity in animals. In particular, the compounds are Central Nervous System depressants and useful, for example, as anticonvulsants as indicated, for example, by inhibition of chemically induced seizures in mice using a minor modification of the method of Orloff et al, Proc. Soc. Exp. Biol., 70 : 254 (1949) on intraperitoneal administration, and by inhibition of maximal electroshock induced convulsion in mice according to the method of Toman et al, J. Neurophysiol 9 : 231 (1946) on the intraperitoneal administration. For such usage, the compounds may be combined with a pharmaceutically acceptable carrier, and such other conventional adjuvants as may be necessary, and administered orally in such forms as tablets, capsules, elixirs, suspensions and the like or parenterally in the form of an injectable solution or suspension. For the above-mentioned uses, the dosage administered will, of course, vary depending upon known factors such as the compounds used and the mode of administration. However, in general, satisfactory results are obtained when administered at a daily dosage of from about 0.5 milligram to about 100 milligrams per kilogram of body weight, preferably given in divided doses 2 to 4 times a day, or in sustained release form. For most mammals the administration of from about 30 milligrams to about 800 milligrams of the compound per day provides satisfactory results and dosage forms suitable for internal administration comprise from about 7 milligrams to about 400 milligrams of the compound in admixture with a solid or liquid pharmaceutical carrier or diluent.

The compounds of the invention may produce responsé in other animal tests indictive of their central nervous system depressant activity and/or indicative of other beneficial activities which may be obtained in combination. For example, the compounds exhibit a mixed central nervous system activity in behavior tests in mice. The compound of Example 4 (evaluated as both free base and as methanesulfonate acid addition salt) is indicted as also useful as a tranquilizer by the muscle relaxant test in mice on administration intrperitoneally essentially according to the method of Dunham et al, J. Am. Pharm. Assoc. 46 : 208 (1957), and by antagonism of amphetamine in mice on administration intraperitoneally. The compound of Example 2, a particularly preferred compound, is also indicated as useful as a tranquilizer/sedative-hypnotic by antagonizing amphetamine, by the muscle relaxant test in mice, by an antagonism of shock-induced agression in mice, and by reinducing hexobarbital anesthesia in mice on administration intraperitoneally.

The additional beneficial pharmacological activities and uses of the particular compounds based on the above-mentioned tests may be realized on administration in the same manner and within the same dosage range previously indicted, with, in the case of the compound of Example 2, the sedative-hypnotic effect being indicated as obtained in mammals in the higher range dosages from about 600 to 800 milligrams per day, and thus accordingly the preferred daily dosage range for the use of the compound of Example 2 as a tranquilizer is from about 30 to 600 milligrams.

For the above uses, the compounds may be combined with a pharmaceutically acceptable carrier, and such other conventional adjuvants as may be necessary, and are preferably administered orally in such forms as tablets, capsules, elixirs, suspensions and solutions. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred pharmaceutical compositions from the standpoint of preparation and ease of administration are solid compositions, particularly hard-filled capsules and tablets.

A representative formulation is a table prepared by conventional tabletting techniques and containing the following ingredients:

| Ingredient | Parts by Weight |
| --- | --- |
| 5-Aminomethyl-5H-dibenzo[a,d]cyclo-hepten-5-ol | 50 |
| Tragacanth | 2 |
| Lactose | 34.5 |
| Corn Starch | 5 |
| Talcum | 3 |
| Magnesium stearate | 0.5 |

The following examples are for purposes of illustration only.

EXAMPLE 1

5-Hydrazinomethyl-5H-dibenzo[a,d]cyclohepten-5-ol.

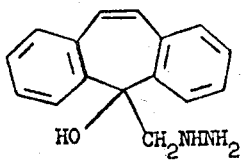

STEP A: Preparation of spiro[dibenzo[a,d]cycloheptene-5,2'-oxirane].

A mixture of 4.6 g. of sodium hydride (57%) and 100 ml. of dimethylsulfoxide is heated under nitrogen at 75° C. for 50 minutes and the resulting mixture treated by addition of 40 ml. tetrahydrofuran and then cooled to 0° C. Over a period of 3 minutes there is then added 10.2 g. of trimethylsulfonium iodide in 100 ml. of dimethylsulfoxide, the resulting mixture stirred for one minute and there is then added over a period of 10 minutes a solution of 16.4 g. of dibenzo[a,d]cyclohepten-5-one in 40 ml. of tetrahydrofuran. The resulting mixture is kept overnight at temperature of 5° C. and then stirred for 3 hours at room temperature (20° C.). The mixture is then poured onto 3 times its volume of ice water, extracted twice each with 600 ml. of pentane, the organic phases combined, washed four times with water, dried over anhydrous sodium sulfate and evaporated in vacuo to crystallize spiro[dibenzo[a,d]cycloheptene-5,2'-oxirane], m.p. 90°–91° C.

STEP B: Preparation of 5-hydrazinomethyl-5H-dibenzo[a,d]cyclo-hepten-5-ol.

A mixture of 10.5 g. of spiro [dibenzo[a,d]cycloheptene-5,2'-oxirane] and 100 ml. of anhydrous hydrazine is refluxed for 3 hours, the resulting mixture evaporated in vacuo to about 50 ml., cooled, the resulting crystals filtered off and washed generously with water. The crude solid is taken up in methylene chloride, extracted with water and then with saturated sodium chloride solution, dried and evaporated in vacuo. The residue is crystallized from ethyl acetate to obtain 5-hydrazinomethyl-5H-dibenzo[a,d]cyclo-hepten-5-ol, m.p. 128°–131° C.

EXAMPLE 2

5-Aminomethyl-5H-dibenzo[a,d]cyclo-hepten-5-ol.

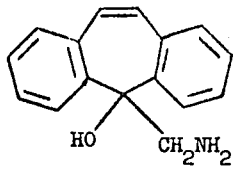

A mixture of 6 g. of 5-hydrazinomethyl-5H-dibenzo[a,d] cyclohepten-5-ol, 160 mg. of platinum dioxide, 60 ml. of ethyl acetate and 60 ml. glacial acetic acid is hydrogenated at room temperature and about atmospheric pressure for 9 hours during which the uptake of hydrogen is about stoichimetric. The resulting mixture is filtered, evaporated in vacuo and the residue treated with 10% sodium bicarbonate solution and then with methylene chloride. The separated aqueous phase is extracted with methylene chloride and the combined organic phases extracted with water and then with saturated sodium chloride solution, followed by drying and evaporation in vacuo. The residue is crystallized from diethyl ether to obtain 5-aminomethyl-5H-dibenzo[a,d] cyclohepten-5-ol, m.p. 117°–120° C.

Additionally prepared following the procedure of Exampe 2 with appropriate conventional modification thereof are:

a. 5-aminomethyl-5H-dibenzo[a,d]cyclohepten-5-ol hydrochloride, mp 224° C. (decomp.) (Crystallized from ethanol/diethyl ether)
b. 5-aminomethyl-5H-dibenzo[a,d]cyclohepten-5-ol benzoate, mp 155°–157° C. (Crystallized from methanol/diethyl ether)
c. 5-aminomethyl-5H dibenzo[a,d]cyclohepten-5-ol methanesulfonate, mp 192°–194° C. (Crystallized from ethanol).

EXAMPLE 3

5-Hydrazinomethyl-10,11-dihydro-5H-dibenzo[a,d]cyclohepten-5-ol.

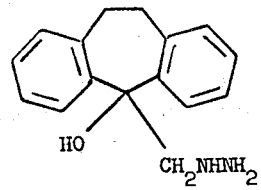

STEP A: Preparation of 10,11-dihydro-spiro[dibenzo[a,d]cyclohepten-5,2'-oxirane]

A mixture of 2.5 g. of sodium hydride (57%) and 45 ml. of dimethylsulfoxide is heated under nitrogen at 75° C. for 50 minutes and the resulting mixture treated by addition of 40 ml. tetrahydrofuran and then cooled to 0° C. Over a period of 3 minutes there is then added 10.2 g. of trimethylsulfonium iodide in 40 ml. of dimethylsulfoxide, the resulting mixture stirred for one minute and there is then added over a period of 10 minutes a solution of 10.4 g. of 10,11-dihydro-dibenzo[2,d] cyclo-hepten-5-one in 50 ml. of dimethylsulfoxice. The resulting mixture is kept overnight at temperature of 5° C. and then stirred for 3 hours at room temperature (20° C.). The mixture is then poured onto 500 ml. of ice water, extracted three times each with 300 ml. of diethyl ether, the organic phases combined, washed five times with water and then with saturated sodium chloride solution. The resulting curde oil is extracted with pentane and crystallized therefrom to obtain 10,11-dihydro-spiro[dibenzo[a,d]cycloheptene-5,2'-oxirane], m.p. 79°–80° C.

STEP B: Preparation of 5-hydrazinomethyl-10,11-dihydro-5H-dibenzo[a,d]cyclo-hepten-5-ol.

A mixture of 10.0 g. of 10,11-dihydro-spiro[dibenzo[a,d] cycloheptene-5,2'-oxirane] and 100 ml. of anhydrous hydrazine is refluxed for 3 hours, the resulting mixture evaporated in vacuo to dryness, the residue dissolved in methanol and again evaporated in vacuo to dryness. The residue is crystallized from diethyl ether to obtain 5-hydrazinomethyl-10,11-dihydro-5H-dibenzo[a,d]cyclo-hepten-5-ol, m.p. 95°–105° C. (decomp.). It was observed that this product decomposed slowly at room temperature to form dibenzo[a,d]cyclohepten- 5-one and thus must be stored at reduced temperatures if to be preserved in relatively pure form for any substantial period of time.

In general, the spiro[dibenzo[a,d]cycloheptene-5,2'-oxiranes] of formula II including the 10,11-dihydro compound are prepared for use in the invention by reacting dimethylsulfonium -methylide (prepared in a known manner) with the appropriate dibenzo[a,d]cyclohepten-5-one at temperatures preferably of from 0° C. to 40° C. in an organic solvent such as dimethylsulfoxide and/or an ether such as diethyl ether, tetrahydrofuran and the like.

EXAMPLE 4

5-Aminomethyl-10,11-dihydro-5H-dibenzo[a,d]cyclohepten-5-ol.

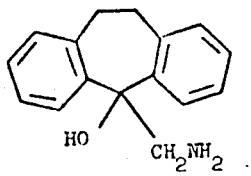

A mixture of 8 g. of freshly prepared 5-hydrazinomethyl-10,11-dihydro-5H-dibenzo[a,d]cyclohepten-5-ol, 40 mg. of platinum dioxide, 120 ml. of ethyl acetate and 40 ml. glacial acetic acid is hydrogenated at room temperature and about atmospheric pressure until the uptake of hydrogen is about stoichiometric. The resulting mixture is filtered, evaporated in vacuo and the residue taken up in 400 ml. of chloroform, made neutral by shaking with 10% sodium bicarbonate solution, and the aqueous phase discarded. The organic phase is extracted twice with water and then with saturated sodium chloride solution, followed by drying and evaporation in vacuo to about 50 ml. to effect crystallization which is completed by adding 50 ml. of diethyl ether to obtain 5-aminomethyl-10,11-dihydro-5H-dibenzo[a,d]cyclohepten-5-ol, m.p. 147°–149° C.

EXAMPLE 5

5-Aminomethyl-5H-dibenzo[a,d]cyclohepten-5-ol

STEP A: Preparation of 5-hydroxy-dibenzo[a,d]cyclohepten-5-acetic acid ethyl ester.

To a suspension of 8.35 g. of activated zinc in 120 ml. of absolute benzene is added at room temperature a solution of 10.3 g. of dibenzo[a,d]cyclohepten-5-one and 8.35 g. of ethyl bromoacetate in 50 ml. of absolute benzene. After about one quarter of said solution has been so added the mixture is heated at reflux until the resulting reaction subsides and then the remainder of the solution is added while maintaining reflux temperatures. After addition is completed the resulting mixture is refluxed for an additional 4 hours. The resulting mixture is then added to dilute acetate acid and extracted 2 times with ethyl acetate. The combined organic phases are washed with water, dried and evaporated in vacuo. The residue is crystallized from diethyl ether/pentane to obtain 5-hydroxy-dibenzo[a,d]cyclohepten-5-acetic acid ethyl ester, m.p. 93°–99° C.

STEP B: Preparation of 5-hydroxy-dibenzo[a,d]cyclohepten-5-acetic acid hydrazide.

A mixture of 4.0 g. of 5-hydroxy-dibenzo[a,d]cyclohepten-5-acetic acid ethyl ester and 8 ml. of anhydrous hydrazine is warmed with stirring at temperature of 80°–85° C. for 2 hours, and then allowed to stand at room temperature for 19 hours. The resulting mixture is evaporated to dryness in high vacuum at 100° C., the residue dissolved in hot ethanol, treated with charcoal and crystallized to obtain 5-hydroxy-dibenzo[a,d]cyclohepten-5-acetic acid hydrazide, m.p. 192°–194° C.

STEP C: Preparation of Spiro(5H-dibenzo[a,d]cyclohepten-5-oxazolin-2-one).

To a separating funnel is charged 3.1 g. of 5-hydroxy-dibenzo[a,d]cyclohepten-5-acetic acid hydrazide, 20 ml. of water, 5 g. of ice, 2 ml. of acetic acid and a solution of 1.6 g. sodium nitrite in 3 ml. of water. The mixture is then shaken for 10 minutes, an additional 2 ml. of acetic acid added and shaking continued for an additional 15 minutes. The resulting mixture is extracted benzene and the benzene layer washed with water, then with sodium bicarbonate solution and then with sodium chloride solution. The resulting benzene solution is then evaporated to dryness on a steam bath and the residue crystallized from 95% ethanol to obtain spiro(5H-dibenzo[a,d]cyclohepten-5-oxazolin-2-one), m.p. 305° C. (decomp. 270° C.)

STEP D: Preparation of 5-aminomethyl-5H-dibenzo[a,d]cyclohepten-5-ol.

A mixture of 1.0 g. of spiro(5H-dibenzo[a,d]cyclohepten-5-oxazolin-2-one), 2.0 g. of potassium hydroxide and 30 ml. of 95% ethanol is refluxed for about 15 hours. The resulting mixture is evaporated in vacuo to dryness and the residue treated with just enough 2N. hydrochloric acid to make neutral. The resulting mixture is extracted with diethyl ether, the ether layer is washed twice with water and once with sodium chloride solution, dried, evaporated in vacuo and the residue crystallized from diethyl ether/pentane and then twice recrystallized from diethyl ether to obtain 5-aminomethyl-5H-dibenzo[a,d]cyclohepten-5-ol, m.p. 117°–120° C.

EXAMPLE 6

Following the procedure of Example 5 the following compounds of the invention are obtained:
a. 5-aminomethyl-7,8-dimethoxy-5H-dibenzo[a,d]cyclohepten-5-ol, m.p. 126°–129° C. (Crystallized from methylene chloride/diethyl ether).
b. 5-aminomethyl-7-chloro-5H-dibenzo[a,d]cyclohepten-5-ol, m.p. 88°–91° C. (Crystallized from diethyl ether).

EXAMPLE 7

5-Methylaminomethyl-5H-dibenzo[a,d]cyclohepten-5-ol

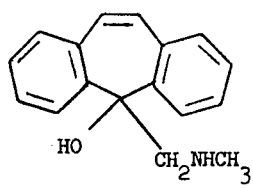

STEP A: Preparation of spiro(5H-dibenzo[a,d]cyclohepten-5-N-methyloxazolin-2-one).

To a stirred suspension of 21 g. of spiro (5H-dibenzo[a,d]cyclohepten-5-oxazolin-2-one) in 400 ml. of dimethylacetamide is added at room temperature 25 g. of sodium hydride (after freeing from mineral oil with diethyl ether). Hydrogen is evolved and a thick precipitate is formed. The resulting mixture is then diluted with 200 ml. of dimethylacetamide and stirred for 2.5 hours. There is then added 20 ml. of methyl iodide and the resulting mixture stirred at room temperature for 2.5 hours. The resulting mixture is concentrated to about 1/2 volume, water/ice slowly added thereto and the crystalline precipitate therein recovered by filtering, washed thoroughly with water and dried by suction. The precipitate is thus dissolved in methylene chloride, dried over sodium sulfate, treated with charcoal and concentrated in vacuo. The liquid residue is treated with diethyl ether to crystallize spiro(5H-dibenzo[a,d]cyclohepten-5-N-methyloxazolin-2-one), m.p. 167°–169° C.

STEP B: Preparation of 5-methylaminomethyl-5H-dibenzo[a,d]cyclohepten-5-ol.

A mixture of 1.0 g. of spiro(5H-dibenzo[a,d]cyclohepten-5-N-methyloxazolin-2-one, 2.0 g. of potassium hydroxide and 35 ml. of 95% ethanol is refluxed for 20 hours. The resulting mixture is evaporated in vacuo to dryness, 2N. hydrochloric acid added to the residue and the resulting mixture filtered. The filtrate is made basic with sodium hydroxide solution, extracted with diethyl ether. The ether extract is washed with water, treated with saturated sodium chloride solution, dried and evaporated in vacuo to dryness. The residue is dissolved in diethyl ether, treated with charcoal and the ether replaced by pentane to crystallize 5-methylaminomethyl-5H-dibenzo[a,d]cyclohepten-5-ol, m.p. 112°–114° C.

What is claimed is:

1. A compound of the formula:

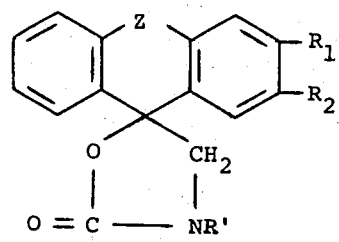

wherein
R' is hydrogen or alkyl of 1 to 4 carbon atoms,
Z is —CH=CH— or —CH$_2$CH$_2$—,
R$_1$ is hydrogen, fluoro, chloro, bromo or alkoxy of 1 to 3 carbon atoms, and
R$_2$ is hydrogen, fluoro, chloro, bromo or alkoxy of 1 to 3 carbon atoms.

2. A compound of claim 1 in which Z is —CH=CH—.
3. A compound of claim 2 in which each of R$_1$ and R$_2$ is hydrogen.
4. The compound of claim 3 in which R' is hydrogen.
5. The compound of claim 3 in which R' is methyl.
6. A compound of claim 2 in which R$_1$ is hydrogen and R$_2$ is chloro.
7. The compound of claim 6 in which R' is hydrogen.
8. A compound of claim 2 in which each of R$_1$ and R$_2$ is alkoxy.
9. A compound of claim 8 in which each of R$_1$ and R$_2$ is methoxy.
10. The compound of claim 9 in which R' is hydrogen.

* * * * *